US006531131B1

(12) United States Patent
Gu et al.

(10) Patent No.: US 6,531,131 B1
(45) Date of Patent: Mar. 11, 2003

(54) CONJUGATE VACCINE FOR NEISSERIA MENINGITIDIS

(75) Inventors: Xin-Xing Gu, Rockville, MD (US); Chao-Ming Tsai, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/626,003

(22) Filed: Jul. 26, 2000

Related U.S. Application Data

(60) Provisional application No. 60/148,021, filed on Aug. 10, 1999.

(51) Int. Cl.$^7$ .................... A61K 39/385; A61K 39/116; A61K 39/102; A61K 39/095; C12P 21/06

(52) U.S. Cl. .................... 424/193.1; 424/194.1; 424/197.11; 424/203.1; 424/234.1; 424/236.1; 424/250.1; 435/68.1

(58) Field of Search .............................. 435/7.32, 68.1; 424/1.73, 9.2, 130.1, 156.1, 179.1, 184.1, 250.1, 193.1, 194.1, 197.11, 203.1, 234.1, 236.1

(56) References Cited

U.S. PATENT DOCUMENTS

| | | | |
|---|---|---|---|
| 4,356,170 A | * | 10/1982 | Jennings et al. |
| 5,013,661 A | | 5/1991 | Munford et al. |
| 5,705,161 A | | 1/1998 | Van Der Ley et al. |
| 6,207,157 B1 | | 3/2001 | Gu et al. |

FOREIGN PATENT DOCUMENTS

| | | |
|---|---|---|
| WO | WO 93/13797 | 7/1993 |
| WO | WO 98/53851 | 12/1998 |

OTHER PUBLICATIONS

Gibson, et al., (1993) Investigation of the Structureal Heterogeneity of Lipooligosaccharides from Pathogenic Haemophilus and Neisseria Species and of R–Type Lipopolysaccharides from *Salmonella typhimurium* by Electrospray Mass Spectrometry. J. of Bacteriology 175(9):2702–2712.

Goldschneider, et al. (1969) Human Immunity to the Miningococcus I. The Role of Humoral Antibodies. Dept. of Bacteriology, Walter Reed Army Inst. of Research, J. Exp. Med. 129:1306–1325.

Gupta, et al. (1995) Comparative Immunogenicity of Conjugates Composed of *Escherichia coli* O111 O–Specific Polysaccharide, Prepared by Treatment with Acetic Acid or Hydrazine, Bound to Tetanus Toxoid by Two Synthetic Schemes. Infection and Immunity 63(8):2805–2810.

Konadu, et al. (1994) Preparation, Characterization, and Immunological Properties in Mice of *Escherichia coli* O157 O–Specific Polysaccharide–Protein Conjugate Vaccines, Infection and Immunology 62(11):5048–5054.

Phillips, et al. (1992) Structural Characterization of the Cells Surface Lipooligosaccharides from a Nontypable Strain of Haemophilus influenzae.

Achtman, M., et al., A comparison of the variable antigens expressed by clone IV–1 and subgroup III of *Neisseria meningitidis* serogroup A. J. Infect. Dis. 165:53–68. 1992.

Anderson, P., Antibody responses to *Haemophilus influenzae* type b and diphtheria toxin induced by conjugates of oligosaccharides of the type b capsule with the nontoxic protein $CRM_{197}$. Infect. Immun. 39(1):233–238. 1983.

Avery, O. T. and Goebel, W. F., Chemo–immunological studies on conjugated carbohydrate–proteins. J. Exp. Med. 54:437–447. 1931.

Beuvery, E., et al., Physicochemical and immunological characterization of meningococcal group A polysaccharide–tetanus conjugates prepared by two methods. Vaccine, 1(1):31–36. 1983.

Beuvery, E., et al., Preparation and immunochemical characterization of the meningococcal group C polysaccharide–tetanus toxoid conjugates as a new generation of vaccines. Infect. Immun. 40(1):39–45. 1983.

Brandtzaeg, P. et al., Plasma endotoxin as a predictor of multiple organ failure and death in systemic meningococcal disease. J. Infect. Dis. 159(2):195–204. 1989.

Chu, C. et al., Further studies on the immunogenicity of *Haemophilus influenzae* type b and pneumococcal type 6A polysaccharide–protein conjugates. Infect. Immun. 40(1):245–256. 1983.

Chu, C., et al., Preparation, characterization, and immunogenicity of conjugates composed of the O–specific polysaccharide of *Shigella dysenteriae* type 1 (*Shiga's bacillus*) bound to tetanus toxoid. Infect. Immun. 59(12):4450–4458. 1991.

Cryz, Jr., S., et al., Safety and immunogenicity of a *Pseudomonas aeruginosa* O–polysaccharide–toxin A conjugate vaccine in humans. J. Clin. Invest. 80:51–56. 1987.

Cryz, Jr., S., et al., Vaccine potential of *Pseudomonas aeruginosa* O–polysaccharide–toxin A conjugates. Infect. Immun. 55(7):1547–1551. 1987.

Cryz, Jr., S., et al., Synthesis and characterization of *Escherichia coli* O18 O–polysaccharide conjugate vaccines. Infect. Immun. 58(2):373–377. 1990.

(List continued on next page.)

Primary Examiner—Mark Navarro
(74) Attorney, Agent, or Firm—Knobbe, Martens, Olson & Bear LLP

(57) ABSTRACT

A conjugate vaccine for *Neisseria meningitidis* comprising lipooligosaccharide which does not contain a lacto-N-tetraose antigen from which at least one primary O-linked fatty acid has been removed conjugated to an immunogenic carrier. The vaccine is useful for prevention of meningitis and septic shock in mammals.

30 Claims, 2 Drawing Sheets

OTHER PUBLICATIONS

Decker, M., et al., Four conjugages Haemophilus b vaccines in infants: a comparative trial, Abstr. 61. Program Abstr. 30$^{th}$ Intersci. Conf. Antimicrob. Agents Chemother. 1990.

Di Fabio, J., et al., Structure of the L1 and L6 core oligosaccharide epitopes of Neisseria meningtidis. Can. J. Chem. 68:1029–1034. 1990.

Dubois, M., et al., Colorimetric method for determination of sugars and related substances. Anal. Chem. 28(3):350–356. 1956.

Erwin, A., et al., Enzymatically deacylated neisseria lipopolysaccharide (LPS) inhibits murine splenocyte mitogenesis induced by LPS. Infec. Immun. 59(6):1881–1887. 1991.

Finne, J., et al., Antigenic similarities between brain components and bacteria causing meningitis. Lancet 355–357 . 1983.

Fox, J. D. and Robyt, J. F., Miniaturization of three carbohydrate analyses using a microsample plate reader. Anal. Biochem. 195:93–96. 1991.

Frasch, C. E. and Robbins, J. D., Protection against group B meningococcal disease. J. Exp. Med. 147:629–644. 1978.

Frasch, C. E., et al., Serotype antigens of Neisseria meningitidis and a proposed scheme for designation of serotypes. Rev. Infect. Dis. 7(4):504–510. 1985.

Frasch, C. E., Prospects for prevention of meningococcal disease: special reference to group B. Vaccine 5:3–4. 1987.

Frasch, C. E., Vaccines for the prevention of meningococcal disease. Clin. Microbiol. Rev. 2 (Suppl.):134–138. 1989.

Goldschneider, I., et al., Human immunity to the meningococcus. I. The role of humoral immunity. J. Exp. Med. 129:1307–1326. 1969.

Goldschneider, I., et al., Human immunity to the meningococcus. II. Development of natural immunity. J. Exp. Med. 129:1327–1349. 1969.

Gotschlich, E. C., et al., Human immunity to the meningococcus. IV. Immunogenicity of group A and group C meningococcal polysaccharides in human volunteers. J. Exp. Med. 129:1367–1384. 1969.

Gu, X. and Tsai, C., Purification of rough–type lipopolysaccharides of Neisseria meningitidis from cells and outer membrane vesicles in spent media. Anal. Biochem. 196:311–318. 1991.

Gu, X. et al., Production and characterization of monoclonal antibodies to type 8 lipopolysaccharide of Neisseria meningitidis. J. Clin. Microbiol. 30(8):2047–2053. 1992.

Gu, X. and Tsai, C., Preparation, characterization, and immunogenicity of meningococcal lipooligosaccharide–derived oligosaccharide–protein conjugates. Infec. Immun. 61(5):1973–1880. 1993.

Gu, X., et al., Synthesis, characterization, and immunologic properties of detoxified lipooligosaccharide from nontypeable haemophilus influenzae conjugated to proteins. Infect. Immun. 64(10):4047–4053. 1996.

Gu, X., et al., Synthesis and characterization of lipooligosaccharide–based conjugates as vaccine candidates for moraxella (branhamella) catarrhalis. Infect. Immun. 66(5):1891–1987. 1998.

Gupta, R., et al., Synthesis, characterization, and some immunological properties of conjugates composed of the detoxified lipopolysaccharide of vibrio cholerae O1 serotype inaba bound to cholera toxin. Infect. Immun. 60(8):3201–3208. 1992.

Hardy, M., et al., Monosaccharide analysis of glycoconjugates by anion exchange chromatography with pulsed amperometric detection. Anal. Biochem. 170:54–62. 1988.

Holton, E., Serotypes of Neisseria meningitidis isolated from patients in Norway during the first six months of 1978. J. Clin. Microbiol. 9(2):186–188. 1979.

Jennings, H., et al., The R–type lipopolysaccharides of Neisseria meningitidis. Can. J. Chem. 58:128–136. 1980.

Jennings, H. J. and Lugowski, C., Immunochemistry of groups A, B, and C meningococcal polysaccharide–tetanus toxoid conjugates. J. Immunol. 127(3):1011–1018. 1981.

Jennings, H., et al., Conjugation of meningococcal lipopolysaccharide R–type oligosaccharides to tetanus toxoid as route to a potential vaccine against group B Neisseria meningitidis. Infect. Immun. 43(1):407–412. 1984.

Jennings, H., et al., Induction of meningococcal group B polysaccharide–specific IgG antibodies in mice by using an N–propionylated B polysaccharide–tetanus toxoid conjugate vaccine. J. Immunol. 137(5):1708–1713. 1986.

Jennings, H., et al., N–propionylated group B meningococcal polysaccharide mimics a unique epitope on groub B Neisseria meningitidis. J. Exp. Med. 165:1207–1211. 1987.

Jennings, H., et al., Structure and immunochemistry of meningococcal lipopolysaccharides. Antoinie van Leeuwenhoek 53:519–522. 1987.

Kemp, H. A. and Morgan, M. R. A., Studies on the detrimental effects of bivalent binding in a microtitration plate ELISA and possible remedies. J. Immunol. Methods 94:65–72. 1986.

Kim, J., et al., Electromorphic characterization and description of conserved epitopes of the lipooligosaccharides of group A Neisseria meningitidis. Infect. Immun. 56(10):2631–2638. 1988.

Konadu, E., et al., Synthesis, characterization, and immunological properties in mice of conjugates composed of detoxified lipopolysaccharide of Salmonella paratyphi A bound to tetanus toxoid, with emphasis on the role of O acetyls. Infect. Immun. 64(7):2709–2715. 1996.

Lambden, P. R. and Heckels, J. E., Synthesis of immunogenic oligosaccharide–protein conjugates from the lipopolysaccharide of Neisseria gonorrhoeae P9. J. Immunol. Methods. 48:233–240. 1982.

Lepow, M., et al., Reactogenicity and immunogenicity of a quadrivalent combined meningococcal polysaccharide vaccine in children. J. Infect. Dis. 154(6):1033–1036. 1986.

Mandrell, R. E. and Zollinger, W. D., Lipopolysaccharide serotyping of Neisseria menigitidis by hemagglutination inhibition. Infect. Immun. 16(2):471–475. 1977.

Mandrell, R., et al., Lipooligosaccharides (LOS) of Neisseria gonorrhoeae and Neisseria meningitidis have components that are immunochemically similar to precursors of human blood group antigens. J. Exp. Med. 168:107–126. 1988.

Michon, F., et al., Structure of the L5 lipopolysaccharide core oligosaccharide of Neisseria meningitidis. J. Biol. Chem. 265(13):7243–7247. 1990.

Peltola, H., Meningococcal disease: still with us. Rev. Infect. Dis. 5(1):71–91. 1983.

Peltola, H., et al. Evaluation of 2 tetravelent (ACYW$_{135}$) meningococcal vaccines in infants and small children: a clinical study comparing immunogenicity of O–acetyl–negative and O–acetyl–positive group C polysaccharides. Pediatrics 76(1):91–96. 1985.

Polotsky, V., et al., Comparison of conjugates composed of lipopolysaccharide from *Shigella flexneri* type 2a detoxified by two methods and bound to tetanus toxoid. Infect. Immun 62(1):210–214. 1994.

Poolman, J., et al., Problems in the definition of meningococcal serotypes. FEMS. Microbiol. Lett. 13:339–348. 1982.

Robbins, A. and Freeman, P., Obstacles to developing vaccines for the Third World. Sci. Am. 259(11):126–133. 1988.

Robbins, J. B. and Schneersch, R., Polysaccharide–protein conjugates: a new generation of vaccines. J. Infect. Dis. 161:821–832. 1990.

Salih, M., et al., Characterization of epidemic and nonepidemic *Neisseria menigitidis* serogroup A strains from Sudan and Sweden. J. Clin. Microbiol. 28(8):1711–1719. 1990.

Schneerson, R., et al., Preparation, characterization, and immunogenicity of *Haemophilus influenzae* type b polysaccharide–protein conjugates. J. Exp. Med. 152:361–376. 1980.

Schneerson, R., et al., Enhancement of the serum antibody response in mice to polysaccharide–protein conjugates by concurrent injection with MPL. J. Immunol. 147(2):2136–2140. 1991.

Seid, Jr., R. C. and Sadoff, J. C., Preparation and Characterization of Detoxified Lipopolysaccharide–protein conjugates. J. Biol. Chem. 256(14):7305–7310. 1981.

Smith, P., et al., Measurement of protein using bicinchoninic acid. Anal. Biochem. 150:76–85. 1985.

Staros, J., et al., Enhancement by N–hydroxysulfosuccinimide of water–soluble carbodiimide–mediated coupling reactions. Anal. Biochem. 156:220–222. 1986.

Svenson, S. B. and Lindberg, A. A., Coupling of acid labile Salmonella specific oligosaccharides to macromolecular carriers. J. Immunol. Methods 25:323–335. 1979.

Svenson, S. B. and Lindberg, A. A., Artificial Salmonella vaccines: *Salmonella typhimurium* O–antigen–specific oligosaccharide–protein conjugates elicit protective antibodies in rabbits and mice. Infect. Immun. 32:490–496. 1981.

Tsai, C., et al., Immunotype epitopes of *Neisseria meningitidis* lipopolysaccharide types 1 through 8. Infect. Immun. 55(7):1652–1656. 1987.

Tsai, C. and Civin, C. I., Eight Lipooligosaccharides of *Neisseria meningitidis* react with a monoclonal antibody which binds lacto–N–neotetraose. Infect. Immun. 59(10):3604–3609. 1991.

Tsai, C., et al. Lipooligosaccharide–based conjugates as potential vaccines for *Neisseria meningitidis* and nontypable *Haemophilus influenzae*. Poster 104, The Fifth Conf. Of The International Endotoxin Society, Santa Fe, New Mexico, Sep. 12–15, 1998.

Verheul, A., et al., Preparation, characterization, and immunogenicity of meningococcal immunotype L2 and L3,7,9 phosphoethanolamide group–containing oligosaccharide–protein conjugates. Infect. Immun. 59(3):843–851. 1991.

Westphal, O. and Jann, K., Bacterial lipopolysaccharides: Extraction with phenol–water and further applications of the procedure. Methods Carbohydr. Chem. 5:83–91. 1965.

Zollinger, W., et al., Human antibody response to three meningococcal outer membrane antigens: Comparison by specific hemagglutination assays. Infect. Immun. 10(5): 975–984. 1974.

Zollinger, W. D. and Mandrell, R. E., Outer–membrane protein and lipopolysaccharide serotyping of *Neisseria meningitidis* by inhibition of a solid–phase radioimmunoassay. Infect. Immun. 18(2):424–433. 1977.

Zollinger, W., et al., Complex of meningococcal group B polysaccharide and type 2 outer membrane protein immunogenic in man. J. Clin. Invest. 63:836–848. 1979.

Zollinger, W. D. and Mandrell, R. E., Type–specific antigens of group A *Neisseria meningitidis*: lipopolysaccharide and heat–modifiable outer membrane proteins. Infect. Immun. 28(2):451–458. 1980.

Baydar et al J Trace Elem Med Biol vol. 13 pp 89–92, 1999.*

* cited by examiner

FIG. 2

Conjugation of detoxified LOS(dLOS) to tetanus toxoid (TT)

A. Oligosaccharide-COOH + $NH_2NH-CO-(CH_2)_4-CO-NHNH_2$
   |
   dLA (lipid A)

dLOS                    ADH (linker)

$\xrightarrow{\text{EDC/Sulfo-NHS}}$ $NH_2NH-CO-(CH_2)_4-CONH-NHCO-Oligosaccharide-dLA$ ADH-dLOS B. Protein-$[COOH]_n$ + ADH-dLOS $\xrightarrow{\text{EDC}}$
   (TT)

Protein-$[CONH-NHCO-(CH_2)_4-CONH-NHCO-Oligosaccharide-dLA]_n$
   (TT)

dLOS-TT conjugate

CONJUGATE VACCINE FOR *NEISSERIA MENINGITIDIS*

RELATED APPLICATIONS

This application claims priority under 35 U.S.C. §119(e) to U.S. Provisional Application Ser. No. 60/148,021, filed Aug. 10, 1999.

FIELD OF THE INVENTION

The present invention relates to a conjugate vaccine for *Neisseria meningitidis* comprising detoxified lipooligosaccharide from which at least one primary O-linked esterified fatty acid has been removed from lipid A linked to an immunogenic carrier. More specifically, the invention relates to a conjugate vaccine against *N. meningitidis* in which the detoxified lipooligosaccharide does not contain the structure of the lacto-N-neotetraose human blood group antigen.

DESCRIPTION OF THE RELATED ART

*Neisseria meningitidis* is a capsulated gram-negative bacterium that causes meningitis and septic shock in humans. In industrialized countries, the annual incidence is 1 to 5 in 100,000, while in nonindustrialized countries, it is estimated that 330,000 persons suffer from meningococcal disease, with 35,000 deaths per year. More than half of the cases occur in children below the age of 5 years, with the highest incidence occurring in the first 2 years. About 90% of the cases are caused by serogroups A, B, and C; the remainder are caused by serogroups Y and W135. Group A dominates in Africa during both epidemic and endemic periods, while group B is the most medically relevant in the United States and Europe.

The sole natural habitat and reservoir for *N. meningitidis* is the human upper respiratory mucosal surface, primarily the nasopharynx. Meningococci are transmitted by large respiratory droplets or direct contact with respiratory secretions. Carriage of the meningococcus in general does not lead to disease. During non-epidemic periods, when disease is rare, 5–30% of the adult population is colonized by the meningococcus which suggests that host rather than bacterial factors determine the outcome.

There are two major problems in the development of vaccines for *N. meningitidis*. First, the current A, C, Y, and W135 capsular polysaccharide (PS) vaccines are less immunogenic in young children, especially infants; and second, group B capsular PS, a polymer of α(2–8)-linked sialic acid which is also present in some human gangliosides and a number of fetal glycoproteins, is poorly immunogenic in humans. The immunogenicity of the capsular PSs can be improved by coupling them to proteins, but this procedure may not be desirable for group B capsular PS because antibodies to the PS may cross-react with human tissue antigens and may cause an autoimmune disease. There is no vaccine against group B meningococcal strains which are the most important disease strains in the United States and Europe.

Lipooligosaccharide (LOS) is a major *N. meningitidis* cell surface antigen. LOS contains both lipid A and oligosaccharide (OS) components. LOS from *N. meningitidis* has twelve immunotypes, L1–L12. Immunotypes L8, L9, L10 and L11 are found within group A meningococci, of which L9, L10 and L11 are prevalent and uniquely associated with this serogroup. Immunotypes L1 to L8 are identified within groups B and C meningococci. Because the lipid A component of LOS is toxic, it is detoxified prior to conjugation to an immunogenic carrier for use in a vaccine. Munford et al. (U.S. Pat. No. 5,103,661) describes removal of secondary O-linked esterified fatty acids from bacterial lipopolysaccharide (LPS) from various Gram negative bacteria, including *N. meningitidis*, by treatment with the enzyme acyloxyhydrolase. This treatment removes two of the four O-linked fatty acid chains from lipid A. The resulting "detoxified" lipid A is only 30–60 fold less toxic than native lipid A (Erwin et al., *Infect. Immun.* 59:1881–1887, 1991), which corresponds to a toxicity of 167–333 IU/μg which is unacceptable for vaccine use as stated in the *W.H.O. Technical Report Series* 814:15–37, 1991 (p. 22, section A.3.3.6).

Hydrazine has been used to detoxify lipid A from various bacterial species, including nontypeable *Haemophilus influenzae* (Gu et al., *Infect. Immun.* 64:4047–4053, 1996), *Shigella* (polotsky et al., *Infect. Immun.* 62:210–214, 1994) and *Moraxella catarrhalis* (Gu et al., *Infect. Immun.* 66:1891–1897, 1998). The resulting detoxified LOS or LPS (dLOS or DeALPS) were conjugated to carrier proteins and their immunogenicities were determined. The hydrazine-detoxified dLOS conjugates from Nontypeable *H. influenzae* and *M. catarrhalis* were immunogenic. However, the hydrazine-detoxified LPS from *Shigella* was poorly immunogenic. Thus, it cannot be predicted whether an LOS or LPS detoxified by hydrazine treatment will be immunogenic.

Thus, there is a need for an effective vaccine against *N. meningitidis*. The present invention addresses this need.

SUMMARY OF THE INVENTION

One embodiment of the present invention is a conjugate vaccine for *Neisseria meningitidis*, comprising *N. meningitidis* lipooligosaccharide which does not contain a lacto-N-neotetraose (LNnT) antigen from which at least one primary O-linked fatty acid has been removed (dLOS), and an immunogenic carrier covalently linked thereto. The conjugate vaccine may also be multivalent, composed of dLOSs from different strains and/or immunotypes of *N. meningitidis*. In another aspect of the present invention, the immunogenic carrier is a protein. Preferably, the protein is tetanus toxin/toxoid, CRM 197, outer membrane proteins from gram negative bacterial pathogens such as high molecular weight proteins, P6 and P4 from nontypeable *Haemophilus influenzae*; CD and USPA from *Moraxella catarrhalis*, diphtheria toxin/toxoid, detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, or respiratory syncytial virus F and G protein. In one aspect of this preferred embodiment, the protein is tetanus toxoid. Advantageously, both primary and secondary O-linked fatty acids have been removed from the lipooligosaccharide.

Another embodiment of the invention is a conjugate vaccine against Group B *N. meningitidis*, comprising at least one, and preferably more than one, LOS(s) isolated from non-Group B immunotypes of *N. meningitidis*, the LOS(s) not containing lacto-N-neotetraose, the LOS(s) detoxified by removing at least one primary O-linked fatty acid, and the detoxified LOS(s) (dLOS) raising antibodies which cross-react with LOS(s) from Group B *N. meningitidis* strains.

The present invention also provides a conjugate vaccine for *N. meningitidis*, comprising *N. meningitidis* lipooligosaccharide which does not contain a LNnT antigen from which at least one O-linked fatty acid has been removed (dLOS), and an immunogenic carrier covalently linked thereto via a linker. Preferably, the linker is adipic acid dihydrazide, ε-aminohexanoic acid, chlorohexanol dimethyl acetal, D-glucuronolactone, cystamine or p-nitrophenylamine; most preferably, the linker is adipic acid dihydrazide.

Another embodiment of the invention is isolated N. meningitidis lipooligosaccharide detoxified by removal of at least one O-linked fatty acid therefrom. Preferably, the detoxified lipooligosaccharide is at least about 5,000 fold less toxic than the lipooligosaccharide as determined using the limulus amebocyte lysate (LAL) assay. In another preferred embodiment, the detoxified lipooligosaccharide is at least about 10,000 fold less toxic than the lipooligosaccharide as determined using the limulus amebocyte lysate (LAL) assay. Preferably, the lipooligosaccharide is detoxified by removal of both primary and secondary O-linked fatty acids.

The present invention also provides a pharmaceutical composition comprising the vaccine conjugates described above in a pharmaceutically acceptable carrier. The pharmaceutical composition may further comprise an adjuvant. Preferably, the adjuvant is alum or monophosphoryl lipid A.

Another embodiment of the invention is a method of producing antibodies which recognize N. meningitidis, comprising administering to an individual an effective antibody-producing amount of the vaccine described above. The route of administration may be intramuscular, subcutaneous, intraperitoneal, intraarterial, intravenous or intranasal; most preferably, the administering step is intramuscular. According to another aspect of this preferred embodiment, the effective dose is between about 10 μg and about 50 μg. The method may further comprise booster injections of between about 10 μg and about 25 μg.

According to another aspect of the invention, there is provided a method of detoxifying lipooligosaccharide from N. meningitidis, comprising removing at least one primary O-linked fatty acid therefrom. Preferably, the ester-linked fatty acid(s) is removed by treating the LOS with hydrazine.

Still another aspect of the present invention is a method of making a conjugate vaccine against N. meningitidis, comprising: removing at least one primary O-linked fatty acid from N. meningitidis lipooligosaccharide which does not contain a LNnT antigen to produce dLOS; and covalently binding the dLOS to an immunogenic carrier. Advantageously, the removing step comprises treatment with hydrazine. The method may further comprise the step of attaching dLOS to a linker and attaching the linker to the carrier. Preferably, the linker is adipic acid dihydrazide, ε-aminohexanoic acid, chlorohexanol dimethyl acetal, D-glucuronolactone, cystamine or p-nitrophenylethyl amine; most preferably, the linker is adipic acid dihydrazide. In one aspect of this preferred embodiment, the dLOS is at least about 5,000 fold less toxic than the lipooligosaccharide as determined using the limulus amebocyte lysate (LAL) assay. In another aspect of this preferred embodiment, the dLOS is at least about 10,000 fold less toxic than the lipooligosaccharide as determined using the LAL assay.

BRIEF DESCRIPTION OF THE DRAWINGS

FIG. 2 shows a reaction scheme for conjugation of detoxified N. meningitidis LOS (dLOS) to tetanus toxoid.

DETAILED DESCRIPTION OF THE PREFERRED EMBODIMENTS

Figure 1:
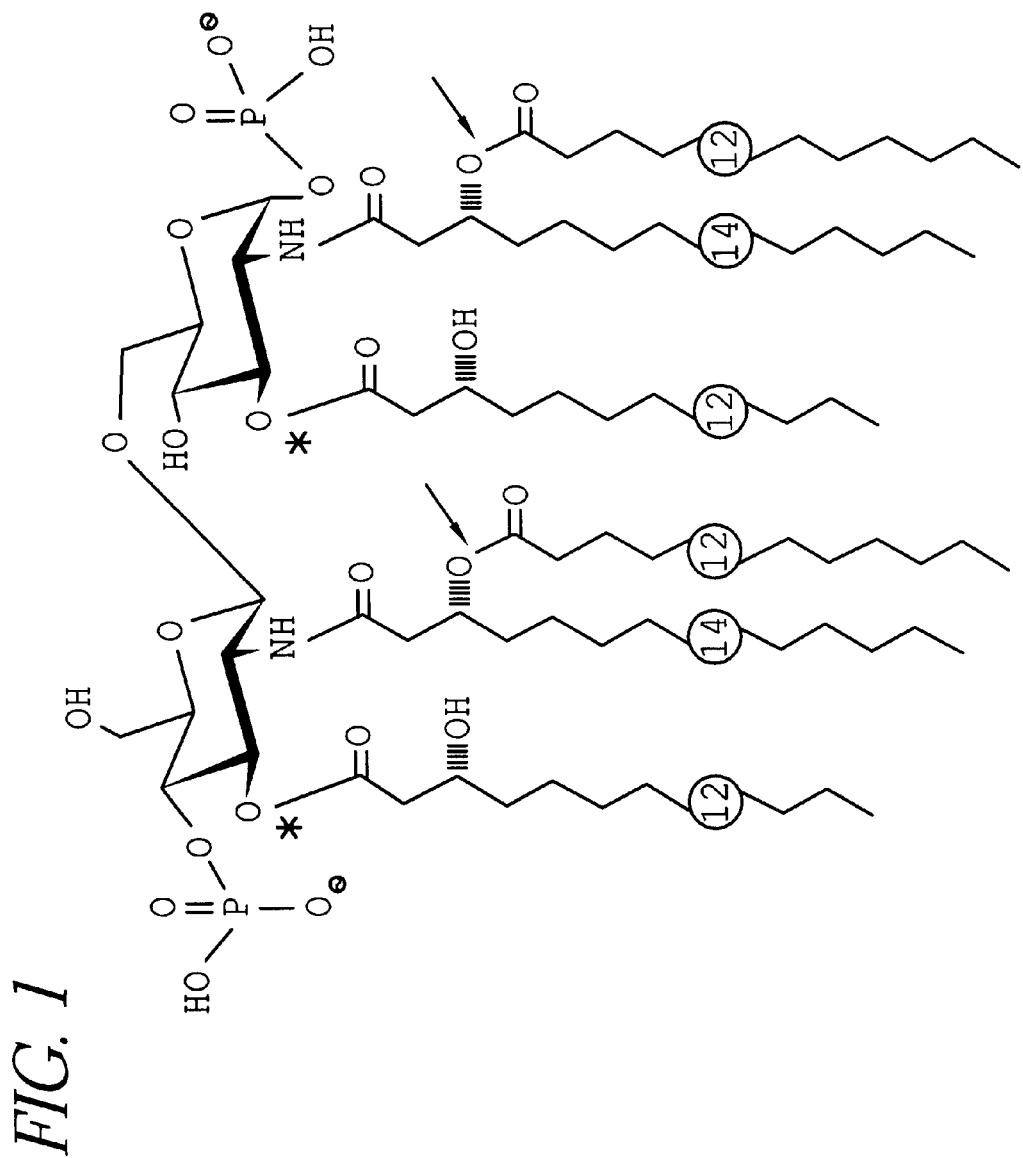
FIG. 1 shows the chemical structure of the lipid A component of N. meningitidis LOS. Hydrazine treatment of LOS removes two primary O-linked fatty acids from 3-hydroxy groups of diglucosamine (*) and two secondary O-linked fatty acids from hydroxy groups of 3-hydroxy fatty acids of lipid A (arrow).

The present invention includes a conjugate vaccine comprising N. meningitidis lipooligosaccharide (LOS) from which at least one primary O-linked esterified fatty acid has been removed (detoxified LOS or dLOS), and an immunogenic carrier. The structure of the lipid A component of N. meningitidis LOS is shown in FIG. 1. The O-linked esterified fatty acids shown by the asterisks are defined as primary O-linked fatty acids and those shown by the arrows are defined as secondary O-linked fatty acids. The conjugate vaccine may also comprise LOS from which both primary O-linked fatty acids have been removed. In addition to the removal of at least one primary O-linked fatty acid from LOS, one or both of the secondary O-linked fatty acids may also be removed. The number of primary and secondary O-linked fatty acids removed by hydrazine treatment, or by treatment with any other reagent capable of hydrolyzing these linkages, will depend on the time and temperature of the hydrolysis reaction. The determination of the number of fatty acid chains which have been removed during the reaction can be determined by standard analytical methods including mass spectrometry and nuclear magnetic resonance (NMR).

The conjugate vaccine in which dLOS was conjugated to tetanus toxoid (TT) induced significant increases in anti-LOS IgG antibody levels in both mice and rabbits. The antisera generated against the dLOS-TT conjugates in rabbits was bactericidal against N. meningitidis as determined by a complement-mediated cell lysis assay. The conjugates exhibited very low toxicity as determined using the limulus amebocyte lysate (LAL) assay and the mouse lethal toxicity test.

Although the use of hydrazine for detoxification of LOS from N. meningitidis is described herein, the use of any reagent or enzyme capable of removing at least one primary O-linked fatty acid from LOS is within the scope of the present invention. For example, other bases such as sodium hydroxide, potassium hydroxide, and the like may be used. The structure of the lipid A component of N. meningitidis LOS is shown in FIG. 1. Dried LOS from one or more strains of N. meningitidis is suspended in liquid anhydrous hydrazine at a temperature of between about 25° C. and 50° C.; more preferably, about 37° C. for a period between 15 minutes and 24 hours, most preferably for a period of about 2–3 hours. After removal of one or more primary O-linked fatty acids, dLOS is conjugated to the linker adipic acid dihydrazide (ADH) prior to conjugation to an immunogenic carrier proteins such as TT (FIG. 2). Although ADH is the preferred linker, the use of any linker capable of stably and efficiently conjugating dLOS to an immunogenic carrier protein is contemplated. The use of linkers is well known in the conjugate vaccine field (see Dick et al., *Conjugate Vaccines*, J. M. Cruse and R. E. Lewis, Jr., eds., Karger, New York, pp. 48–114, 1989, the entire contents of which are hereby incorporated by reference).

dLOS may be directly covalently bonded to the carrier. This may be accomplished, for example, by using the cross linking reagent glutaraldehyde. However, in a preferred embodiment, dLOS and the carrier are separated by a linker. The presence of a linker promotes optimum immunogenicity of the conjugate and more efficient coupling of the dLOS with the carrier. Linkers separate the two antigenic components by chains whose length and flexibility can be adjusted as desired. Between the bifunctional sites, the chains can contain a variety of structural features, including heteroatoms and cleavage sites. Linkers also permit corresponding increases in translational and rotational characteristics of the antigens, increasing access of the binding sites to soluble antibodies. Besides ADH, suitable linkers include, for example, heterodifunctional linkers such as ε-aminohexanoic acid, chlorohexanol dimethyl acetal, D-glucuronolactone and p-nitrophenyl amine. Coupling reagents contemplated for use in the present invention include hydroxysuccinimides and carbodiimides. Many other linkers and coupling reagents known to those of ordinary skill in the art are also suitable for use in the invention (e.g. cystamine). Such compounds are discussed in detail by Dick et. al., supra.

The presence of a carrier increases the immunogenicity of the dLOS. In addition, antibodies raised against the carrier may be medically beneficial. Polymeric immunogenic carriers can be a natural or synthetic material containing a primary and/or secondary amino group, an azido group or a carboxyl group. The carrier may be water soluble or insoluble.

Any one of a variety of immunogenic carrier proteins may be used in the conjugate vaccine of the present invention. Such classes of proteins include pili, outer membrane proteins and excreted toxins of pathogenic bacteria, nontoxic or "toxoid" forms of such excreted toxins, nontoxic proteins antigenically similar to bacterial toxins (cross-reacting materials or CRMs) and other proteins. Nonlimiting examples of bacterial toxoids contemplated for use in the present invention include tetanus toxin/toxoid, diphtheria toxin/toxoid, detoxified *P. aeruginosa* toxin A, cholera toxin/toxoid, pertussis toxin/toxoid and *Clostridium perfringens* exotoxins/toxoid. The toxoid forms of these bacterial toxins is preferred. The use of viral proteins (i.e. hepatitis B surface/core antigens; rotavirus VP 7 protein and respiratory syncytial virus F and G proteins) is also contemplated.

CRMs include CRM197, antigenically equivalent to diphtheria toxin (Pappenheimer et al., *Immunochem.,* 9:891–906, 1972) and CRM3201, a genetically manipulated variant of pertussis toxin (Black et al., *Science,* 240:656–659, 1988). The use of immunogenic carrier proteins from non-mammalian sources including keyhole limpet hemocyanin, horseshoe crab hemocyanin and plant edestin is also within the scope of the invention.

Outer membrane proteins include high molecular weigh proteins (HMPs), P4 and P6 from nonteypeable *Haemophilus influenzae* and CD and USPA from *Moraxella catarrhalis*. For a list of other outer membrane proteins, see PCT WO098/53851, the entire contents of which are hereby incorporated by reference.

There are many coupling methods which can be envisioned for dLOS-protein conjugates. In the examples set forth below, dLOS is selectively activated by 1-ethyl-3-(3-dimethylaminopropyl)carbodiimide (EDC)-mediated ADH derivatization of the terminal 3-deoxy-D-manno-2-octulosonic acid (KDO) group of dLOS, followed by EDC-mediated coupling to TT. Alternatively, another method for producing the instant conjugates involves cystamine derivatization of dLOS, by, for example, EDC-mediated derivatization, followed by disulfide conjugation to N-succimidyl-3-(2-pyridyldithio)propionate-derivatized protein. Other methods well known in the art for effecting conjugation of oligosaccharides to immunogenic carrier proteins are also within the scope of the invention. Such methods are described in, for example, U.S. Pat. Nos. 5,153,312 and 5,204,098; EP 0 497 525; and EP 0 245 045, the entire disclosures of which are hereby incorporated by reference.

The molar ratio of ADH to dLOS in the reaction mixture is typically between about 10:1 and about 250:1. A molar excess of ADH is used to ensure more efficient coupling and to limit dLOS-dLOS coupling. In a preferred embodiment, the molar ratio is between about 50:1 and about 150:1; in a most preferred embodiment, the molar ratio is about 100:1. Similar ratios of AH-dLOS to both TT and HMP in the reaction mixture are also contemplated. In a preferred embodiment, one ADH per dLOS is present in the AH-dLOS conjugate. In another preferred embodiment, in the final dLOS-carrier protein conjugate, the molar ratio of dLOS to carrier is between about 15 and about 75, preferably between about 25 and about 50.

Immunogenicity of the conjugates in both mice and rabbits is enhanced by the use of monophosphoryl lipid A plus trehalose dimycolate (Ribi-700; Ribi Immunochemical Research, Hamilton, Mont.) as an adjuvant. Although this adjuvant is not approved for use in humans, the skilled artisan will appreciate that other well known standard adjuvants may be used in the invention, including aluminum compounds (i.e. alum), monophosphoryl lipid A (in the absence of trehalose dimycolate), chemically-modified lipopolysaccharide, suspensions of killed *Bordetella pertussis*, N-acetylmuramyl-L-alanyl-D-glutamine and other adjuvants known to one of ordinary skill in the art. The use of aluminum compounds is particularly preferred. Such adjuvants are described by Warren et al. (*Ann. Rev. Biochem.,* 4:369–388, 1986), the entire disclosure of which is hereby incorporated by reference.

The dLOS-carrier protein conjugates for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed, including synthetic mono- or diglycerides. In addition, fatty acids such as oleic acid may likewise be used in the preparation of injectable preparations.

The conjugate vaccine of the invention may be in soluble or microparticular form, or may be incorporated into microspheres or microvesicles, including liposomes. Although various routes of vaccine administration including, for example, intramuscular, subcutaneous, intraperitoneal and intraarterial are contemplated, the preferred route is intramuscular administration. In a preferred embodiment, the dosage of the conjugate administered will range from about 10 μg to about 50 μg. In a more preferred embodiment, the amount administered will be between about 20 μg and about 40 μg. In a most preferred embodiment, the amount administered is about 25 μg. Greater doses may be administered on the basis of body weight. The exact dosage can be determined by routine dose/response protocols known to one of ordinary skill in the art.

The vaccine of the invention may be administered to individuals of any age and are adapted to induce active immunization in young children, preferably infants, against meningitis and septic shock caused by *N. meningitidis*. As a childhood vaccine, the conjugate is administered at about 2 to 4 months of age. Typically, two booster injections of between about 10 μg and about 25 μg are administered at about 2 and again about 13 months after the initial injection. Alternatively, three booster injections are given at 2, 4 and 16 months after the initial injection.

The IgG antibodies elicited by systemic administration of the conjugate vaccine will transfer to local mucosa and inactivate N. meningitidis inoculum on mucosal surfaces (i.e., nasal passages). Secretory IgA will also play a role in mucosal immunity if the conjugate vaccine is administered directly to the mucosa (i.e. intranasally). Direct mucosal administration of the conjugate vaccine of the invention to the mucosa is also within the scope of the present invention. In a preferred embodiment, when administered to the mucosa, the conjugate vaccine is combined with an adjuvant such as *Escherichia coli* heat labile exotoxin LTB which is a less toxic mutated form of cholera toxin which is known to boost mucosal immunity. Thus, the conjugate vaccine will prevent local, as well as systemic, N. meningitidis infection.

The examples describe conjugate vaccines using N. meningitidis strain 7880. Vaccines from other N. meningitidis strains are also within the scope of the present invention and are made using the same techniques. The medically relevant strains of N. meningitidis belong to serogroups A, B, C, Y and W135. Each of these strains is associated with one or more immunotype(s) of LOS, L1–L12. N. meningitidis strain 7880 belongs to group A and has LOS immunotype L10 (A, L10). Numerous N. meningitidis strains are available from the American Type Culture Collection (ATCC), including ATCC 33086, 23248, 23250, 23583 and 23247. N. meningitidis strains contemplated as sources of LOS for generation of a dLOS-carrier conjugate vaccine include any strain which does not contain an epitope recognized as a human antigen, such as the LNnT antigen described below. These strains include 7880 (L10), A1 (L8), 7889 (L11), 7897 (L12) and other strains which are either obtainable from ATCC, or are generally available from the research community.

Meningococcal LOS immunotypes are not related to serogroups and a given LOS type may be found in different serogroups. For example, a group A strain may share a LOS immunotype with a group B strain, i.e. cross-react. For the 12 LOS types (L1–L12), L1 to L8 are found mostly in groups B and C, and L9 to L12 are in group A. The predominant LOS type in the group B disease strains is L3. However, L3 and many other LOS immunotypes in group B contain the structure of lacto-N-neotetraose (LNnT), a precursor of human blood group antigens, and is recognized as self. Thus, an immune response to these immunotypes is not likely to occur. Even if an immune response to a LOS immunotype containing this self antigen did occur, this would most likely be deleterious because of autoimmune reactions. Thus, in a preferred embodiment, LOS(s) devoid of structures recognized as human antigens, particularly the LNnT structure, is used to prepare the conjugate vaccines of the invention. The LOSs which contain the LNnT structure can be determined using the anti-My-28 monoclonal antibody as described by Tsai et al. (*Infect. Immun.* 59:3604–3609, 1991, incorporated by reference).

Unlike antibodies to serogroups, antibodies to a LOS are usually cross-reactive. For example, although 7880 (L10) is a group A strain, antibodies to this LOS cross-reacted with L5, L7 and L8 LOSs which were found in group B organisms (see Example 9). It is contemplated that the conjugate vaccine will be a multivalent vaccine comprising a mixture of two or more conjugates, each having a dLOS from a different N. meningitidis strain. In a preferred embodiment, the dLOS chosen to be part of the vaccine composition does not contain the human LNnT antigen and cross-reacts with LOS from strains belonging to group B. The LOS-based conjugate vaccines of the invention will protect against Group B N. meningitidis strains, the most important disease strains in the U.S. and Europe, and may also be effective against other groups which share the immunotype of the LOS(s) used in the vaccine.

A Group B N. meningitidis conjugate vaccine of the invention would comprise at least one, and preferably more than one, dLOS isolated from different strains and/or immunotypes, the dLOS(s) not containing the LNnT antigen, and the dLOS(s) raising antibodies that cross-react with LOS from Group B strains. The number and identity of strains from which the LOS is isolated and which are part of a multivalent vaccine is determined empirically. The object is to maximize the number of Group B strains and/or immunotypes which cross-react with antisera raised against the vaccine. Tsai et al. (supra.) teach how to avoid LOSs with the LNnT antigen, and Example 9 demonstrates how cross-reactivity with Group B LOSs is determined. The same can be done with any LOS isolated from any N. meningitidis strain.

In a preferred embodiment, the dLOS moieties thus obtained are at least about 5,000 fold less toxic than LOS itself. In a particularly preferred embodiment, the dLOSs are at least about 10,000 fold less toxic than dLOS. Determination of toxicity may be performed, for example, according to Example 8 below.

N. meningitidis strain 7880 was grown and LOS was isolated as described in the following example.

EXAMPLE 1

Bacterial Growth and LOS Purification

N. meningitidis strain 7880 (Zollinger et al., *Infect. Immun.* 28:451–458, 1980) was grown on chocolate agar plates in a 5% $CO_2$ atmosphere at 37° C. for 8 hours, then transferred to 200 ml tryptic soy broth (Difco, Detroit, Mich.). The medium was placed in an incubator shaker set at 150 rpm and 37° C. overnight. The culture broth was transferred to five 2.8 l flasks, each containing 1.4 liters TSB media. Flasks were shaken at 140 rpm at 37° C. for 24 hours. The culture broth was centrifuged at 15,000×g for 30 minutes to separate cells and supernatant.

LOS was purified from cells by the classical phenol-water extraction method with modification (Westphal et al., *Meth. Carbohyd. Chem.*, 5:83–91, 1965, incorporated by reference). Briefly, cells were grown overnight and treated with 90% phenol (45% final concentration) at 68–70° C. for 15–20 min., cooled on ice and centrifuged. After recovery of the upper aqueous phase, the remainder was re-extracted with water. Sodium acetate (5 mg/ml) was added to the combined aqueous phases and the LOS was precipitated with 2 volumes of acetone to reduce phospholipid contamination. The pellets were washed twice with 70% ethanol to reduce trace phenol, then dissolved in water. RNase and DNase were added (50–100 µg/ml) and samples were incubated at 37° C. for 3–5 hours. Proteinase K (0.5 mg/ml) was then added and the samples were incubated at 60° C. overnight, then centrifuged at least twice at 150,000×g for 3 hours. The gel-like LOS was dissolved in about 10 volumes of water and lyophilized.

LOS was also purified from the culture supernatant by gel filtration (Gu et al., *Anal. Biochem.*, 196:311–318, 1991, incorporated by reference). Briefly, 6–8 liters of culture supernatant were concentrated to 100–200 ml using a hollow-fiber cartridge with a 100,000 molecular weight cutoff (Amicon, Danvers, Mass.). To the concentrate was added 5–10 volumes of water, followed by reconcentration to about 400 ml. LOS containing outer membrane vesicles (OMV) were then pelleted by ultracentrifugation at 150,000×g and suspended in water to a 5–10% (v/v) suspension. To 10 ml of an opalescent OMV suspension, EDTA was added to a concentration of 2 mM, and the pH adjusted to 8.5 with 1 M NaOH. Sodium deoxycholate (Na-DOC) (2%, w/v) was added and the mixture was kept at 37° C. for 10 minutes to solubilize LOS from OMV. LOS was separated from outer membrane proteins on a 5×90 cm Sephacryl S-300 column (Pharmacia) using 20 mM Tris, pH 8.5, 2 mM EDTA, 1% sodium deoxycholate (Na-DOC), 0.02% sodium azide as an elution buffer. Proteins were monitored by absorbance at 280 nm.

LOS could be detected as ethanol precipitable materials as follows. To 200 µl aliquots of the column fractions, 3 volumes of ethanol (95%) were added after adjusting the aliquots to 0.25 M NaCl with 5 M NaCl. The mixtures were vortexed and LOS immediately precipitated. According to the LOS precipitation, the main LOS fractions were pooled, precipitated in 70% ethanol overnight as described above and collected by low speed centrifugation. LOS was dissolved in water to about 10 mg/ml for another cycle of ethanol precipitation to reduce residual Na-DOC, proteins and phospholipids, then washed with 70% ethanol, lyophilized and weighed.

The protein and nucleic acid content of purified LOS from both cells and culture supernatant was less than 1%. The LOS purified from cells and from culture supernatant was combined and detoxified as described below.

EXAMPLE 2

Detoxification of LOS

LOS (160 mg), isolated as described in Example 1, was dried over phosphorus pentoxide ($P_2O_5$) for 3 days, suspended in 16 ml anhydrous hydrazine (Sigma) and incubated at 37° C. for 2 hours, mixing every 15 min. The solution was placed on ice, then added dropwise to cold acetone in an ice bath until a precipitate formed ($\geq$90% acetone). The mixture was centrifuged at 5,000×g at 5° C. for 30 min. The pellet was washed twice with cold acetone, dissolved in pyrogen-free water to 20 mg/ml, and centrifuged at 150,000×g for 3 hours at 5° C. The supernatant was lyophilized and applied to a 1.6 ×90 cm SEPHADEX® G-50 gel filtration column (Pharmacia, Upssala, Sweden). The column was eluted with 25 mM ammonium acetate and monitored with a differential refractometer (R-400; Waters, Milford, Mass.). The eluate was assayed for carbohydrate content by the phenol-sulfuric acid method (Dubois et al., *Anal. Biochem.*, 28:250–256, 1956) and the carbohydrate fractions were pooled, lyophilized three times to remove the salt and designated dLOS.

After hydrazine treatment of LOS, the yield of dLOS ranged from 40% to 60% by weight for strain 7880. Sodium dodecyl sulfate-polyacrylamide gel electrophoresis (SDS-PAGE) analysis of LOS and dLOS followed by silver staining showed that the mobility of dLOS is different from that of LOS due to the removal of ester-linked fatty acids.

dLOS was derivatized with ADH as described in the following example.

EXAMPLE 3

Derivatization of dLOS

ADH was bound to the carboxyl group of the KDO moiety of dLOS to form AH-dLOS derivatives using EDC and N-hydroxysulfo-succinimide (sulfo-NHS) (Pierce, Rockford, Ill.) (FIG. 2). dLOS (70 mg) was dissolved in 7 ml of 345 mM ADH (Aldrich, Milwaukee, Wis.) in water. The molar ratio of ADH to dLOS was about 100 to 1. Solid sulfo-NHS was added to a final concentration of 8 mM. The pH was adjusted to 4.8 with 1 M HCl and EDC was added to a concentration of 0.1 M. The reaction mixture was stirred and maintained at pH 4.8±0.2 with 1 M HCl for three hours at room temperature. The reaction mixture was adjusted to pH 7.0 and applied to the G-50 column.

The eluate containing AH-dLOS was assayed for carbohydrate (dLOS) content using dLOS as a standard, then calculated as moles using a molecular weight of 2,500. The amount of AH in AH-dLOS was measured by a modified TNBS method using ADH as a standard and measuring absorbance at $OD_{490nm}$ (Kemp et al., *J Immunol. Meth.*, 94:65–72, 1986).

The peaks containing both carbohydrate and AH were pooled, lyophilized three times to remove the salt, and designated as AH-dLOS. AH-dLOS was measured for its composition using dLOS and ADH as standards. The final molar ratio of AH to dLOS in the AH-dLOS product=moles of AH/moles of dLOS. For strain 7880, the molar ratio of AH to dLOS was 0.27–0.4. The yield for strain 7880, on the basis of carbohydrate content, was 100%.

AH-dLOS was conjugated to TT as described in the following example.

EXAMPLE 4

Conjugation of AH-dLOS to Tetanus Toxoid

AH-dLOS was coupled to carboxyl groups on TT at pH 5.6 with EDC. AH-dLOS (20 mg) was dissolved in 2 ml distilled water and mixed with 10 mg TT (5.9 mg/ml) (Connaught Labs, Inc., Swiftwater, Pa.). The molar ratio of AH-dLOS to TT was about 100 to 1. The pH was adjusted to 5.4 with 0.2 M HCl, followed by addition of EDC to a concentration of 0.05–0.1 M. The reaction mixture was stirred and maintained at pH 5.4±0.2 with 0.1 M HCl for 1 to 3 hours at room temperature or 4° C. The reaction mixture was adjusted to pH 7.0, centrifuged at 1,000×g for 10 min and purified using a 1.6×90 cm SEpHACRYL® S-300 gel filtration column (Pharmacia) equilibrated with 0.9% NaCl. The eluate was monitored for protein by determining $OD_{280}$ of the column fractions and assayed for carbohydrate content. Column fractions containing both protein and carbohydrate were pooled and designated as dLOS-TT. dLOS-TT conjugates were analyzed for carbohydrate and protein using dLOS and BSA as standards. For strain 7880, the molar ratio of dLOS to TT was 30:1 (range=24–32) and the yield was 10–17%. The ratio is expressed as moles of dLOS per mole of TT using a molecular weight of 3,000 for dLOS and 150,000 for TT.

The immunogenicity of the dLOS-TT conjugates was determined as described in the following example.

EXAMPLE 5

Immunogenicity of dLOS-TT Conjugates

The immunogenicity of the *N. meningitidis* 7880 dLOS-TT conjugates was tested in both mice and rabbits. Five week old general purpose mice (NIH/Swiss, female), ten mice per group, were subcutaneously immunized with 5 µg (based on LOS or dLOS weight) of: dLOS-TT, LOS or dLOS plus TT (10 µg) in 0.2 ml 0.9% NaCl with or without Ribi-700 adjuvant containing 50 µg monophosphoryl lipid A and 50 μg synthetic trehalose dimycolate. Mice were injected three times at three week intervals and bled 14 days after the first injection and seven days after the second and third injections.

New Zealand white rabbits (female, 2–3 kg), 2–3 rabbits per group, were subcutaneously immunized with 50 μg dLOS, LOS or dLOS-TT (carbohydrate weight) in 1 ml 0.9% NaCl with or without Ribi-700 adjuvant. Rabbits were injected twice at one-month intervals and bled two weeks after the first injection and 11–14 days after the second injection.

Serum anti-LOS levels were expressed in ELISA units, using *N. meningitidis* 7880 LOS as a coating antigen and *N. meningitidis* 7880 hyperimmune serum as a reference assigned values of 3,000 and 4 units/ml for IgG and IgM, respectively (mouse) and 3,000 and 3 units/ml for IgG and IgM, respectively (rabbit). Serum TT antibody was measured by ELISA in which TT (5 μg/ml) was used as a coating antigen and a horse anti-TT serum (20 IU/ml) as a reference assigned a value of 3,000 units/ml and 3 units/ml for IgG and IgM, respectively. Antibody levels are expressed as the geometric mean in ELISA units of n independent observations ± standard deviation or range (n<4).

In mice, a mixture of dLOS and TT (unconjugated) did not elicit LOS antibodies. The antibody response to LOS elicited by the conjugates is summarized in Table 1. dLOS-TT elicited low LOS IgG levels after the first injection which increased 3- and 4-fold after the second and third injections, respectively. LOS alone elicited low IgG levels after the first injection which increased 2- and 4-fold after the second and third injections, respectively.

The immunogenicity of the conjugates was significantly enhanced by Ribi adjuvant. One dose elicited higher IgG levels than did three doses of the conjugates alone. After three injections, about a six-fold increase in IgG was observed (Table 1). The conjugates elicited minimal, if any, IgM after each injection. Ribi adjuvant enhanced IgM levels in the conjugate groups. As used in all tables set forth herein, "adjuvant" is Ribi-700 adjuvant.

TABLE 1

Murine antibody response to *N. meningitidis* 7880 LOS elicited by conjugates

| Immunogen | Injection No. | No. of mice | Geometric mean ± SD, units/ml* | |
|---|---|---|---|---|
| | | | IgG | IgM |
| LOS | 1 | 5 | 6 (4–10) | 5 (3–8) |
| | 2 | 5 | 11 (4–29) | 7 (3–17) |
| | 3 | 10 | 25 (10–62) | 7 (2–28) |
| dLOS-TT | 1 | 5 | 3 (3–4) | 2 (1–3) |
| | 2 | 5 | 8 (2–25) | 3 (2–7) |
| | 3 | 10 | 12 (3–47) | 5 (2–14) |
| dLOS + TT | 1 | 5 | 4 (3–4) | 2 (1–4) |
| | 2 | 5 | 3 (2–3) | 1 (1–2) |
| | 3 | 10 | 3 (2–4) | 2 (1–3) |
| dLOS-TT + adjuvant | 1 | 5 | 20 (6–56) | 8 (5–13) |
| | 2 | 5 | 251 (86–732) | 15 (12–20) |
| | 3 | 10 | 122 (54–275) | 11 (7–16) |

*one unit is defined as an $A_{405}$ reading of 1 at 30 minutes in ELISA.

One or two rabbits for each group were subcutaneously immunized on days 0 and 28 with 50 μg dLOS, LOS conjugates or conjugates plus Ribi adjuvant. Blood samples were collected on days 0,14 and 38–42. dLOS itself did not elicit anti-LOS antibodies in rabbits. dLOS-TT elicited a significant increase in IgG levels after the first and second injections (81 to 845-fold). Ribi adjuvant enhanced IgG levels elicited by dLOS-TT after the second injection. Both conjugates, either alone or with adjuvant, elicited almost no IgM after each injection. The results are summarized in Table 2.

TABLE 2

Rabbit antibody response to *N. meningitidis* LOS elicited by conjugates

| Immunogen | Injection No. | No. of rabbits | Geometric mean (range) ELISA units/ml | |
|---|---|---|---|---|
| | | | IgG | IgM |
| LOS | Preimmune | 2 | .7 (.47–1.06) | .2 (.1–.3) |
| | 1 | | 2.3 (1.71–3.15) | .2 (.11–.40) |
| | 2 | | 4.9 (3.68–6.65) | .3 (.22–.36) |
| | 3 | | 10 (6.35–15.68) | .5 (.16–1.44) |
| dLOS | Preimmune | 1 | 1.2 | .3 |
| | 1 | | 1.6 | .3 |
| | 2 | | .7 | .3 |
| | 3 | | .9 | .2 |
| dLOS-TT | Preimmune | 2 | 1 (1–3) | .2 (.08–.31) |
| | 1 | | 81 (61–106) | .2 (.10–.48) |
| | 2 | | 845 (471–1519) | .5 (.47–.49) |
| | 3 | | 728 (372–1426) | .4 (.09–1.54) |
| dLOS-TT + adjuvant | Preimmune | 2 | 4 (3–6) | .3 |
| | 1 | | 201 (74–549) | .5 (.46–.58) |
| | 2 | | 2032 (1955–2111) | .5 (.48–.51) |
| | 3 | | 3777 (1912–7462) | .8 (.50–1.39) | dLOS itself did not elicit TT antibodies in rabbits. dLOS-TT elicited anti-TT IgG after the first injection which rose significantly after the second injection. IgG levels were enhanced by adjuvant 4-fold after the second injection. The conjugate, either alone or with adjuvant, elicited low IgM levels after each injection. The results are summarized in Table 3.

TABLE 3

Rabbit antibody response to tetanus toxoid elicited by dLOS-TT conjugates

| Immunogen | Injection No. | No. of rabbits | Geometric mean (range) ELISA units | |
|---|---|---|---|---|
| | | | IgG | IgM |
| LOS | Pre-immune | 2 | .7 (.47–1.06) | .2 (.1–.3) |
| | 1 | | 2.3 (1.71–3.15) | .2 (.11–.40) |
| | 2 | | 4.9 (3.68–6.65) | .3 (.22–.36) |
| | 3 | | 10 (6.35–15.68) | .5 (.16–1.44) |
| dLOS | Pre-immune | 1 | 1.3 | 1.7 |
| | 1 | | 1.36 | 1.4 |
| | 2 | | 1.3 | 1.9 |
| | 3 | | 1.7 | 1.9 |
| dLOS-TT | Pre-immune | 2 | 0.8 (.49–1.25) | .6 (.41–.73) |
| | 1 | | 15 (11–22) | 1.2 (1.13–1.24) |
| | 2 | | 940 (366–2416) | 1.3 (1.21–1.38) |
| | 3 | | 2228 (1481–3350) | 1.3 (1.21–1.41) |
| dLOS-TT + adjuvant | Pre-immune | 2 | 0.8 (.39–1.52) | 1 (.92–1.18) |
| | 1 | | 221 (163–298) | 1.5 (1.05–2.03) |
| | 2 | | 3998 (3760–4250) | 1.5 (1.41–1.58) |
| | 3 | | 4645 (4598–4694) | 1.5 (1.45–1.59) |

EXAMPLE 6

Limulus Amebocyte Lysate (LAL) Assay

Los, dLOS conjugates were diluted with pyrogen-free water. Equal volumes (100 μl) of samples and Limulus amebocyte lysate were mixed and incubated at 37° C. for 1 hour. Gelation of the lysate at the minimal LOS concentration was determined by inverting the mixture. A firm gel was considered a positive reaction (Hochstein et al., *Bull Parenteral Drug Assoc.*, 27:139–148, 1973). All reagents were from the U.S. Food and Drug Administration, Bethesda, Md. The sensitivity of the LAL assay is 0.09 EU per ml. By the LAL assay, the LOS from strain 7880 had the LAL reactivity at 24,800 EU/μg, while the dLOS exhibited this reactivity at 1.5 EU/μg. Thus, dLOS was about 16,000 fold less active than untreated LOS in promoting LAL gelation. According to the W. H. O., this level of toxicity is acceptable for use in a conjugate vaccine.

EXAMPLE 7

Mouse Lethal Toxicity Test

LOS and dLOS from strain 7880 were tested by a mouse lethality assay (Galanos et al., *Proc. Natl. Acad. Sci. USA*, 76:5939–5943, 1979). Briefly, female seven week old inbred BALB/c mice, 4 per group, were injected intraperitoneally with 8 mg D-galactosamine HCl (Sigma) dissolved in 0.2 ml pyrogen-free water (400 mg/kg). Within 30 min., the animals were given different amounts of the experimental preparations in 0.2 ml water by intravenous route. Lethality was observed over a four day period and the $LD_{50}$ was calculated. The results for various amounts of LOS and dLOS are shown in Table 4.

The $LD_{50}$ of dLOS was 30 μg, while the $LD_{50}$ of LOS was between 1 and 2.5 ng. Thus, dLOS was at least 12,000 fold less toxic than untreated LOS.

TABLE 4

Lethal toxicity of *N. meningitidis* 7880 LOS before and after hydrazine detoxification in galactosamine-sensitized BALB/c mice.

| Dose | 0.05 ng | 0.1 ng | 0.5 ng | 1 ng | 2.5 ng | 5 ng |
|---|---|---|---|---|---|---|
| 7880 LOS | 4/4* | 4/4 | 4/4 | 4/4 | 1/4 | 1/4 |
| Dose | 1 μg | 5 μg | 10 μg | 20 μg | 30 μg | 50 μg |
| 7880 dLOS | 4/4 | 3/4 | 4/4 | 3/4 | 2/4 | 0/4 |

*number survived/number treated

EXAMPLE 8

Bactericidal Assay of dLOS-TT Rabbit Antisera

Bactericidal activity of dLOS-TT antisera was based on a modification of a microbactericidal assay (Frasch et al., *J. Exp. Med.*, 147:629–644, 1978; Jennings et al., *J. Exp. Med.*, 165:1207–1221, 1987), the entire contents of which are hereby incorporated by reference. Rabbit preimmune and postimmune sera obtained after two injections of dLOS-TT *N. meningitidis* strain 7880 conjugate were inactivated at 56° C. for 30 min. and tested for bactericidal activity against *N. meningitidis* strains 7880, 6275, M981, 6155 and 44/76. Briefly, serial twofold dilutions of the sera were made in Dulbecco's PBS containing calcium, magnesium, and 0.1% gelatin (DPBSG), such that 50 μl sera or diluted sera were present in each well of a sterile 96-well plate. *N. meningitidis* strains were grown on chocolate agar plates at 37° C., 5% $CO_2$ overnight and 3–5 colonies were transferred to another plate and incubated for 4.5 hours. Bacteria were diluted in DPBSG, and 30 μl bacterial suspension (about $3 \times 10^3$ CFU/ml) were added to each well. Infant rabbit serum (15 μl/well) was added as a source of complement (pel-Freez, Brown Deer, Wis.). Plates were incubated at 37° C. for 30 min. Fifty μl of the mixture was removed from each well and spread on chocolate agar plates (100×15 mm) which were then incubated at 37° C., 5% $CO_2$ overnight and colonies were counted. Controls included complement, inactive complement and a positive serum. The results are shown in Table 5.

TABLE 5

Bactericidal activity of 7880 dLOS-TT antisera

| | | Bactericidal titers for strain[b] | | | | |
|---|---|---|---|---|---|---|
| Immunogen | Antiserum (rabbit no.) | 7880 (A, L10) | 6275 (B, L3) | M981 (B, L5) | 6155 (B, L7) | 44/76 (B, L3, 8) |
| LOS | 72086[a] | 64 | ± | 16 | 8 | 8 |
| dLOS-TT | 1866 | 64 | ± | 16 | 16 | 16 |
| | 1868 | 16 | NT | NT | NT | NT |
| dLOS-TT + adjuvant | 1869 | 64 | NT | NT | NT | NT |

Postimmune sera after three injections were used
[a]LOS antiserum obtained with Freund's adjuvant.
[b]Expressed as the fold increase over the preimmune sera resulting in ≥ 50% killing of each strain.
NT: Not tested
±: no increase over preimmune sera The highest serum dilution causing a >50% killing was expressed as the reciprocal bactericidal titer. The immune sera also exhibited bactericidal activity against the strains M981, 6155 and 44/76, showing that a LOS conjugate isolated from a non-Group B strain can raise bactericidal antibodies against Group B strains.

EXAMPLE 9

Cross-reactivity of 7880 dLOS-TT Antisera with LOS L1–L12

LOS types L1–L12 were isolated from various *N. meningitidis* strains and conjugated to TT as described above. The LOS type and corresponding bacterial strain are shown in Table 6. An ELISA was performed using 7880 polyclonal antisera to determine whether it cross-reacted with any other type of LOS. As shown in Table 6, the 7880 dLOS-TT antisera cross-reacted strongly with three strains from serogroup B having L5, L7 and L8 (M981, 6155 and M978, respectively), indicating that one or more epitopes on LOS immunotypes L5, L7 and L8 from these strains is recognized by an antiserum against serogroup A. In addition, some cross reactivity was observed with L12 from strain 7897, which is in serogroup A. Thus, a dLOS conjugate vaccine may be effective against a plurality of LOS types, against other strains of the same serogroup, and against other serogroups. Western blot analysis using the same immunosera confirmed these ELISA results.

TABLE 6

Cross-reactivity of rabbit antisera to 7880 (L10) dLOS-TT conjugate with 12 N. meningitidis LOSs in ELISA ($A_{405nm}$)

| LOS | L1 | L2 | L3 | L4 | L5 | L6 | L7 | L8 | L9 | L10 | L11 | L12 |
|---|---|---|---|---|---|---|---|---|---|---|---|---|
| Strain | 126E | 35E | 6275 | 89I | M981 | M992 | 6155 | M978 | M120 | 7880 | 7889 | 7897 |
| Serogroup | C | C | B | C | B | B | B | B | A | A | A | A |
| Pre-serum | .08 | .10 | .09 | .09 | .12 | .11 | .12 | .09 | .10 | .12 | .11 | .06 |
| dLOS-TT (rabbit #1866) | .11 | .12 | .06 | .11 | 1.11 | .09 | .92 | .87 | .13 | 2.60 | .14 | .55 |
| dLOS-TT + adjuvant (rabbit #1869) | .21 | .10 | .10 | .21 | .70 | .07 | .44 | .61 | .16 | 2.31 | .18 | .37 |

EXAMPLE 10

Immunization of Humans with dLOS-TT Conjugate

Individuals are intramuscularly administered either 25 μg of the conjugate dLOS-TT vaccine prepared as described in Examples 1–4 or a control vaccine. Boosters of 20 μg of conjugate or control vehicle are intramuscularly administered at 2, 4 and 15 months after the initial injection. Immunogenicity and bactericidal activity of the resulting antisera are determined in accordance with Examples 6 and 9. The frequency of occurrence of meningitis is then monitored over several years. The individuals receiving the conjugate vaccine have significantly fewer episodes of meningitis than the control subjects.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. An immunogenic composition against *Neisseria meningitidis*, comprising *N. meningitidis* lipooligosaccharide (LOS) which does not contain a lacto-N-neotetraose (LNnT) antigen from which at least one primary O-linked fatty acid has been removed to produce detoxified LOS (dLOS), and an immunogenic carrier covalently linked thereto.

2. The composition of claim 1, wherein said immunogenic carrier is a protein.

3. The composition of claim 2, wherein said immunogenic carrier protein is selected from the group consisting of tetanus toxin/toxoid, bacterial outer membrane proteins, CRM197, diphtheria toxin/toxoid, detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, and respiratory syncytial virus F and G protein.

4. The composition of claim 3, wherein said immunogenic carrier protein is tetanus toxoid.

5. The composition of claim 1, wherein said dLOS and said immunogenic carrier are covalently linked by a linker.

6. The composition of claim 5, wherein said linker is selected from the group consisting of adipic acid dihydrazide, ε-aminohexanoic acid, chlorohexanol dimethyl acetal, D-glucuronolactone, cystamine and p-nitrophenylethyl amine.

7. The composition of claim 6, wherein said linker is adipic acid dihydrazide.

8. The composition of claim 1, wherein both primary and both secondary O-linked fatty acids have been removed from said lipooliglsaccharide.

9. Isolated *N. meningitidis* lipooligosaccharide (LOS) detoxified by removal of at least one primary O-linked fatty acid therefrom to produce detoxified LOS (dLOS) conjugated to a carrier.

10. The isolated detoxified lipooligosaccharide of claim 9, wherein both primary and both secondary O-linked fatty acids are removed from said lipooligosaccharide.

11. The detoxified lipooligosaccharide of claim 9, wherein said detoxified lipooligosaccharide is at least 5,000 fold less toxic than said lipooligosaccharide as determined using the limulus amebocyte lysate (LAL) assay.

12. The detoxified lipooligosaccharide of claim 9, wherein said detoxified lipooligosaccharide is at least 10,000 fold less toxic than said lipooligosaccharide as determined using the limulus amebocyte lysate (LAL) assay.

13. A composition comprising the immunogenic composition of claim 1 in a pharmaceutically acceptable carrier.

14. The composition of claim 13, further comprising an adjuvant.

15. The composition of claim 14, wherein said adjuvant is alum or monophosphoryl lipid A.

16. A method of producing antibodies which recognize *N. meningitidis* in an individual, comprising administering to said individual an effective antibody-producing amount of the immunogenic composition of claim 1.

17. The method of claim 16, wherein said composition is administered by a route selected from the group consisting of intramuscular, subcutaneous, intraperitoneal, intraarterial, intravenous and intranasal.

18. The method of claim 17, wherein said administering step is intramuscular.

19. The method of claim 16, wherein said effective antibody-producing amount is between about 10 μg and about 50 μg.

20. The method of claim 16, further comprising one or more booster injections of between about 10 μg and about 25 μg after said administering step.

21. A method of detoxifying lipooligosaccharide (LOS) from *N. meningitidis*, comprising removing at least one primary O-linked fatty acid therefrom to produce detoxified LOS (dLOS), and conjugating said dLOS to a carrier.

22. The method of claim 21, wherein both primary and secondary O-linked fatty acids are removed from said lipooligosaccharide.

23. The method of claim 21, wherein said removing step comprises treatment with hydrazine.

24. A method for making a immunogenic composition against *N. meningitidis*, comprising:

removing at least one primary O-linked fatty acid from an *N. meningitidis* lipooligosaccharide (LOS) which does not contain a lacto-N-neotetraose (LNnT) antigen to produce detoxified LOS (dLOS); and covalently binding said dLOS to an immunogenic carrier.

25. The method of claim 24, wherein said removing step comprises treatment with hydrazine.

26. The method of claim 24, further comprising the step of attaching said dLOS to a linker and attaching said linker to said carrier.

27. The method of claim 26, wherein said linker is selected from the group consisting of adipic acid dihydrazide, ε-aminohexanoic acid, chlorohexanol dimethyl acetal, D-glucuronolactone, cystamine and p-nitrophenylethyl amine.

28. The method of claim 27, wherein said linker is adipic acid dihydrazide.

29. The immunogenic composition of claim 1, wherein said dLOS is at least 5,000 fold less toxic than said lipooligosaccharide as determined using the limulus amebocyte lysate (LAL) assay.

30. The immunogenic composition of claim 1, wherein said dLOS is at least 10,000 fold less toxic than said lipooligosaccharide as determined using the limulus amebocyte lysate (LAL) assay.

* * * * *

UNITED STATES PATENT AND TRADEMARK OFFICE
CERTIFICATE OF CORRECTION

PATENT NO.    : 6,531,131 B1
DATED         : March 11, 2003
INVENTOR(S)   : Xin-Xing Gu and Chao-Ming Tsai It is certified that error appears in the above-identified patent and that said Letters Patent is hereby corrected as shown below:

<u>Title page,</u>
Item [73], Assignee, please correct to read:
-- The Government of the United States of America, as represented by the Secretary, Department of Health and Human Services"

Signed and Sealed this

Ninth Day of March, 2004

JON W. DUDAS
*Acting Director of the United States Patent and Trademark Office*